United States Patent [19]

Hofer et al.

[11] 4,308,218

[45] Dec. 29, 1981

[54] ARYL PHOSPHONITES AND THIOPHOSPHONITES USEFUL AS ANTIOXIDANTS

[75] Inventors: Kurt Hofer, Münchenstein; Rudolf Moesch, Stein; Guenther Tscheulin, Frick, all of Switzerland

[73] Assignee: Sandoz Ltd., Basel, Switzerland

[21] Appl. No.: 154,143

[22] Filed: May 29, 1980

Related U.S. Application Data

[63] Continuation of Ser. No. 66,110, Aug. 13, 1979, abandoned, which is a continuation-in-part of Ser. No. 934,771, Aug. 18, 1978, abandoned.

[30] Foreign Application Priority Data

Aug. 19, 1977 [CH] Switzerland .................... 10201/77

[51] Int. Cl.$^3$ .............................................. C07F 9/48
[52] U.S. Cl. ................................ 260/945; 260/951; 260/958; 260/962
[58] Field of Search ........................... 260/945, 94 R

[56] References Cited

U.S. PATENT DOCUMENTS 4,238,422 12/1980 Cozens et al. ................. 260/940 X

*Primary Examiner*—Anton H. Sutto
*Attorney, Agent, or Firm*—Gerald D. Sharkin; Richard E. Vila; Joseph J. Borovian

[57] ABSTRACT

Aryl phosphonites and thiophosphonites of the formula,

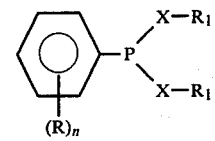

in which
the or each R, independently, is alkyl, alkoxy, chlorine or dialkylamino, there being at the most one dialkylamino group, at the 4-position and unaccompanied by any other substituents, on the benzene nucleus,
n is zero, 1, 2 or 3,
each X, independently, is oxygen or sulphur,
and each $R_1$, independently, is alkyl or optionally substituted phenyl, are useful as antioxidants. Organic material, e.g. polypropylene, which are susceptible to the degradative effects of oxygen, are treated with one or more of such compounds, e.g. by incorporation into the body of the organic material, in order to be stabilized against such effects.

4 Claims, No Drawings

ARYL PHOSPHONITES AND THIOPHOSPHONITES USEFUL AS ANTIOXIDANTS

This is a continuation of application Ser. No. 66,110 filed Aug. 13, 1979, which in turn is a continuation-in-part of Ser. No. 934,771, filed Aug. 18, 1978, both now abandoned.

The present invention relates to aryl phosphonites and thiophosphonites and a process for stabilising organic materials therewith.

Accordingly, the present invention provides a process for stabilising organic materials susceptible to the degradative effects of oxygen against such effects comprising treating said material with a stabilising-effective amount of one or more compounds of formula I,

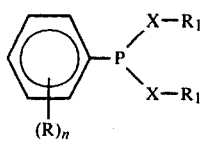

in which
each R independently, is $(C_{1-12})$alkyl, $(C_{1-9})$alkoxy, chlorine or $-N(R_o)_2$ wherein each $R_o$ independently, is $(C_{1-8})$alkyl with the proviso that the total number of carbon atoms in such alkylamino group is less than 11,
n is zero, 1, 2 or 3,
each X, independently, is oxygen or sulphur,
and each $R_1$, independently, is $(C_{1-22})$alkyl; unsubstituted phenyl; or phenyl substituted with up to three substituents selected from 1 to 3 $(C_{1-9})$alkyl radicals, said alkyl radicals having an aggregate of carbon atoms not exceeding 12, a cyclohexyl radical, and an optionally substituted phenyl radical selected from an unsubstituted phenyl radical and a mono-$(C_{1-4})$alkyl-substituted phenyl radical, with the provisos
(i) that when n is 2 or 3, any R is other than $-N(R_o)_2$, and when n is 1 and R is a group $-N(R_o)_2$, this group is in the 4-position of the benzene nucleus, and
(ii) that when n is zero, or when n is 1 and R is alkyl, alkoxy or chlorine, each $R_1$, independently, is a group of formula (a)

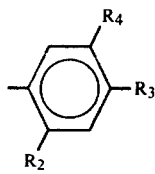

wherein
$R_2$ is $(C_{1-8})$alkyl, cyclohexyl or unsubstituted phenyl,
$R_3$ is hydrogen, $(C_{1-8})$alkyl, cyclohexyl, unsubstituted phenyl or mono-$(C_{1-4})$ alkyl-substituted phenyl,
and $R_4$ is hydrogen or methyl, with the proviso that where one of $R_2$ or $R_3$ is cyclohexyl or optionally substituted phenyl the other has a significance other than cyclohexyl or optionally substituted phenyl.

When R is alkyl, this is preferably $(C_{1-9})$alkyl, more preferably $C_1$ or $C_4$ alkyl, especially methyl or tert.-butyl, and most preferably tert.-butyl.

When R is alkoxy, this is preferably $(C_{1-4})$alkoxy, and more preferably methoxy.

When R is the group $-N(R_o)_2$ each $R_o$ therein, independently, is preferably $(C_{1-4})$alkyl, more preferably $(C_{1-3})$ alkyl, and most preferably methyl or ethyl. Both alkyl radicals are preferably identical.

Of all the significances of R, alkyl, alkoxy or the group $-N(R_o)_2$, especially R', as hereinafter defined, are preferred, alkyl or the group $-N(R_o)_2$, especially R'', as hereinafter defined, are more preferred, and the group $-N(R_o)_2$ is most preferred.

n is preferably zero or 1, and each X, independently, is preferably oxygen. Preferably both X's have the same meaning.

When any $R_1$, independently, is alkyl, this is preferably $(C_{1-18})$ alkyl, more preferably $(C_{4-18})$ alkyl, and most preferably $(C_{8-18})$ alkyl.

When $R_2$ in any group of formula (a), independently, is alkyl, this is preferably methyl or a secondary or tertiary $(C_{3-8})$alkyl radical, more preferably methyl, tert.-butyl, tert. amyl or 1,1-dimethylpropyl, even more preferably methyl, tert.-butyl or tert. amyl, and most preferably tert.-butyl.

Of all the significances of $R_2$, alkyl and unsubstituted phenyl are preferred, and alkyl, especially $R_2'$, as hereinafter defined, more especially methyl, tert.-butyl, tert.-amyl or 1,1-dimethylpropyl, even more especially methyl, tert.-butyl, or tert. amyl, and most especially tert.-butyl, is more preferred.

When $R_3$ in any group of formula (a), independently, is alkyl, this is preferably methyl or a secondary or tertiary $(C_{3-8})$alkyl radical, and more preferably methyl, tert.-butyl or tert. amyl, most preferably methyl or tert.-butyl.

Of all the significances of $R_3$, hydrogen, allkyl and optionally substituted phenyl are preferred, and hydrogen and alkyl are more preferred, especially $R_3'$, as hereinafter defined, and more especially $R_3''$, as hereinafter defined.

$R_4$ in any group of formula (a), independently, is preferably hydrogen.

The group of formula (a) is preferably one of formula (aa), as hereinafter defined.

Of all the significances of $R_1$, $R_1'$, as hereinafter defined, is preferred, and optionally substituted phenyl is more preferred. When, however, either X is oxygen and n is 1, 2 or 3, $R_1$ attached to that X is preferably a group of formula (a) and more preferably a group of formula (aa), more especially a group of formula (a) or (aa), respectively, in which $R_2$ or $R_2'$, respectively, is a secondary or tertiary alkyl radical.

In general, both moieties $R_1$ preferably have the same meaning.

A preferred class of compounds of formula I is constituted by the compounds of formula Ia,

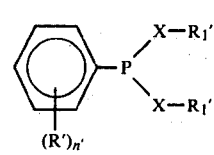

in which
R' is $(C_{1-9})$ alkyl, $(C_{1-9})$ alkoxy or the group $-N(R_o')_2$,
wherein each $R_o'$, independently, is $(C_{1-3})$ alkyl,
n' is zero or 1,
both X's are the same and are oxygen or sulphur,
and both $R_1'$'s are the same and are $(C_{4-18})$ alkyl; unsubstituted phenyl; or phenyl substituted with up to 3 substituents selected from 1 or 2 $(C_{1-9})$ alkyl radicals, said alkyl radicals having an aggregate of carbon atoms not exceeding 9, and an optionally substituted phenyl radical selected from an unsubstituted phenyl radical and a mono-$(C_{1-4})$ alkyl-substituted phenyl radical,
with the provisos
(i) that when R' is the group $-N(R_o')_2$, this group can only occupy the 4-position of the benzene nucleus,
and (ii) that when n is zero, or when n is 1 and R' is alkyl or alkoxy, $R_1'$ can only be a group of formula (aa),

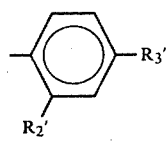

(aa)

wherein
$R_2'$ is methyl or a secondary or tertiary $(C_{3-8})$ alkyl radical,
and $R_3'$ is hydrogen, methyl or a secondary or tertiary $(C_{3-8})$ alkyl radical.

A preferred class of compounds of formula Ia is constituted by the compounds of formula Ib,

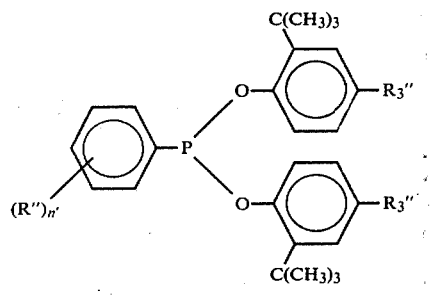

Ib in which
R'' is methyl, tert.-butyl or the group $-N(R_o'')_2$, wherein both $R_o'''$'s are the same and are $(C_{1-3})$ alkyl,
n' is zero or 1,
and both $R_3'''$'s are the same and are hydrogen, methyl or tert.-butyl,
with the proviso that when R'' is the group $-N(R_o'')_2$, this group can only occupy the 4-position of the benzene nucleus.

A further preferred class of compounds of formula I is constituted by the compounds of formula I',

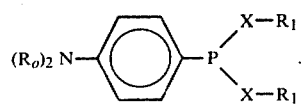

I' in which each $R_o$, each X and each $R_1$, independently, is as defined above.

Of the compounds of formula I', a particular class is constituted by the compounds of formula I'',

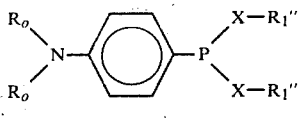

I'' in which
each $R_o$, and each X, independently, is as defined above,
and each $R_1''$, independently, is $(C_{1-18})$ alkyl; unsubstituted phenyl; or phenyl substituted with 1 to 3 alkyl radicals, said alkyl radicals having an aggregate of carbon atoms not exceeding 12.

The present invention further provides compounds of formula $I_x$,

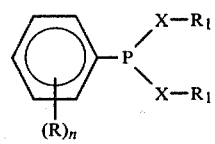

$I_x$ in which
R, $R_1$, n and X are as defined above for the compounds of formula I
with the provisos
($i_x$) that when n is 2 or 3 any R is other than $-N(R_o)_2$ and when R is a group $-N(R_o)_2$ such group is in the 4-position of the benzene nucleus and any alkyl as $R_1$ is $(C_{4-18})$alkyl,
($ii_x$) that when n is zero or when n is 1, 2 or 3 and R is alkyl, alkoxy or chlorine, each $R_1$, independently is a group of formula ($a_x$)

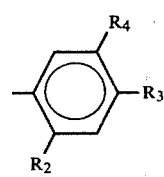

($a_x$)

where $R_2$ $R_3$ and $R_4$ are as defined above with the proviso that when $R_3$ and $R_4$ are both hydrogen $R_2$ is a sec. or tert. $(C_{3-8})$alkyl radical and when one of $R_2$ and $R_3$ is cyclohexyl or optionally substituted phenyl the other is other than cyclohexyl or optionally substituted phenyl.

Preferred compounds of formula $I_x$ are those of formula $I_a$ as defined above, except that $R_2'$ is a secondary or tert. alkyl radical expecially those wherein $R_2'$ is t. butyl or t. amyl and $R_3'$ is hydrogen, methyl t. butyl or t. amyl and those of formula I' wherein each $R_1$, independently, is $R_1'$ as defined above. More preferred compounds of formula $I_x$ are those of formula $I_b$ and I'' wherein any alkyl as $R_1''$ is $(C_{4-18})$alkyl.

The present invention further provides a process for the production of compounds of formula $I_x$ as defined above, comprising reacting a compound of formula II

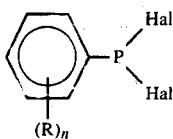

in which
R and n are as defined above,
and Hal is chlorine or bromine,
with a compound or mixture of compounds of formula III, $$R_1XH \qquad \qquad III$$

in which X and $R_1$ are as defined above.

The intermediates of formula II can be produced in known manner from available starting materials, e.g. by reaction of a compound of formula IV,

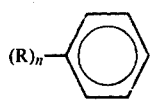

in which R and n are as defined above, with phosphorus trichloride. When $(R)_n$ is a group $-N(R_o)_2$, the reaction is generally performed by boiling the reactants together, optionally in the presence of a suitable solvent, under reflux. In the other cases, such a procedure is generally augmented by the use of a Lewis acid catalyst, e.g. aluminum trichloride.

The intermediates of formula III are either known or can be produced in analogous manner to the known compounds from available starting materials.

The conditions for reacting the compounds of formulae II and III are known from analogous reactions involving the elimination of hydrogen halide from phosphorus halides and alcohols, phenols, mercaptans or thiophenols. Preferably the elimination reaction is carried out in the presence of an acid binding agent, e.g. a tertiary amine or calcium oxide.

The present invention further provides a method of stabilizing an organic material susceptible to the degradative effects of oxygen against such effects comprising treating said material with a stabilizing-effect amount of one or more compounds of formula I, as defined above. By the term treating, as used herein, is meant either incorporating into the body of the organic material, or surface coating the organic material, e.g. in a manner known per se, of which the former mode of treating is preferred for the preferred organic materials to be treated, i.e. polymeric organic materials.

Suitable organic materials which are stabilized by the method of the present invention include such plastics materials as polyolefins, e.g. polyethylene and polypropylene, polystyrene, polyesters, polymethyl methacrylates, polyphenylene oxides, polyurethanes, polyamides, e.g. nylon, polypropylene oxide, polyacrylonitrile, copolymers and terpolymers of the aforementioned polymers, polypyrrolidone, and such natural materials as natural rubber.

The compounds of the present invention are especially suitable for stabilizing polyethylene, polypropylene, polyesters, polyurethanes, polyamides, polyacrylonitrile, copolymers of styrene and acrylonitrile and of styrene and butadiene, and terpolymers of acrylonitrile, butadiene and styrene (ABS) and of acrylic ester, styrene and acrylonitrile, more particularly polyethylene, polypropylene and (ABS) terpolymers, and most particularly polyethylene and polypropylene.

According to an embodiment of the method of the present invention, the compound of formula I is intimately mixed with a plastics material, e.g. polypropylene, preferably in particulate (granulate) form and preferably in a kneader or other suitable mixing device, to obtain even distribution of the compound in the substrate. The treated material may then be formed into final shape, e.g. by extrusion to form, e.g. films, tubings or fibres.

The polymeric organic materials need not necessarily be in the final polymerised or condensed form before being treated with the compounds of the present invention. Thus, according to a second embodiment of the method of the present invention, particularly suited to the stabilization of polymeric or copolymeric materials, the compound of formula I is mixed with the appropriate monomer or prepolymer and/or precondensate before polymerisation or condensation is effected.

The suitable amount of stabilizing compound of formula I employed in the method of the present invention will naturally depend on several factors, e.g. the mode of application, the particular compound employed and the nature of the organic material to be treated. However, when the compound is incorporated into the body of the organic material, satisfactory results are generally obtained when the amount of compound employed is in the range 0.01 to 1% of the weight of the organic material to be treated. Preferably, however, the amount is in the range 0.1 to 0.4%.

The organic materials may also be treated with other additives besides the compounds of formula I to improve their properties, e.g. other stabilizers or costabilizers against the degradative effects of oxygen, heat and/or u.v. light. Particularly preferred additives are distearyl thiodipropionate, tetrakis(methylene-3-dodecylthiopropionate)methane and sterically-hindered 4-methyl- or 4-ethyl-6-tert.-butylphenol or 4,4'-methylenebis-(2,6-di-tert.-butyl phenol). The relative proportion by weight of the compound(s) of formula I to such additives in the method of the present invention is preferably in the range 1:5 to 5:1, more preferably 1:3 to 4:1, e.g. 1:3, respectively.

The present invention further provides an organic material whenever treated according to the method of the present invention, as well as any suitable composition containing one or more compounds of formula I, as defined above, for use in the method of the present invention. Such compositions, which may be referred to as master batches, generally comprise 50 to 90% by weight of the compound, or mixture of compounds of formula I, and a part of the substrate to be treated by the method of the present invention. The use of such a master batch in the method avoids the necessity for those practising the method to initially make up the composition according to recommended ratio specifications before addition to the substrate to be stabilized. The master batch composition is readily worked into or applied onto the main body of the substrate by virtue of the presence of the same substrate in the master batch composition.

In the following Examples, which illustrate the present invention, the parts and percentages are by weight and the temperatures are in degrees Centigrade.

EXAMPLE 1

A mixture of 26 parts of N,N-dimethylaniline and 13.7 parts of phosphorus trichloride is heated for 8 hours under reflux. Then 15.8 parts of pyridine and 130 parts of toluene are added, and the mixture is cooled to 40° and treated dropwise with 41.2 parts of 2,4-di-tert.-butylphenol while stirring. The mixture at 40° is stirred for a further 5 hours, cooled to 0° and filtered to remove precipitated pyridine hydrochloride. Evaporation of the filtrate under reduced pressure affords an oil, which is subsequently dissolved in diethyl ether. The ethereal solution is washed with water, dried over Glauber's salt, and evaporated under reduced pressure to afford a yellow oil. This is crystallized from methanol, yielding white crystals, m.p. 150°–152°, of the product of formula,

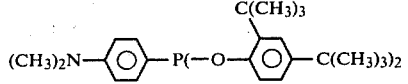

| Analysis %: | C | H | N | O | P |
|---|---|---|---|---|---|
| found | 76.9 | 9.6 | 2.4 | 5.6 | 5.7 |
| calculated | 77.0 | 9.3 | 2.5 | 5.7 | 5.8 |

EXAMPLE 2

The procedure described in Example 1 is repeated using 32.8 parts of 2-tert.-butyl-4-methylphenol instead of 41.2 parts of 2,4-di-tert.-butylphenol. Produced is the compound of formula,

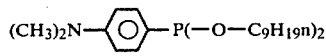

in the form of white crystals, m.p. 116°–120°.

| Analysis %: | C | H | N | O | P |
|---|---|---|---|---|---|
| found | 75.5 | 8.6 | 3.0 | 7.1 | 6.6 |
| calculated | 75.5 | 8.4 | 2.9 | 6.7 | 6.5 |

EXAMPLES 3–5

In an analogous manner to that described in Example 1, the following compounds of formula I are produced from the appropriate starting materials

| Example | Structure |
|---|---|
| 3 | 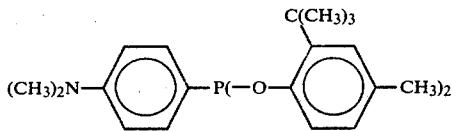 |
| 4 | 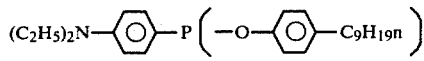 |
| 5 | 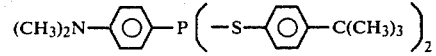 |

EXAMPLE 6

To a mixture of 123.6 parts of 2,4-di-tert.-butylphenol, 52.1 parts of pyridine and 120 parts of acetic acid at 0° are added dropwise, over a period of one hour, 53.7 parts of dichlorophenyl phosphine. After completion of the addition, the reaction mixture is allowed to react further for 2 hours at room temperature and for 17 hours at 40°. Then it is cooled to 0° and the white precipitate is collected by filtration, washed with water and dried in vacuo at 60°. The product, m.p. 92°–93°, consists of the compound of formula,

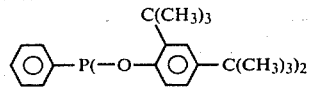

| Analysis %: | C | H | P |
|---|---|---|---|
| found | 78.6 | 9.0 | 5.9 |
| calculated | 78.7 | 9.1 | 6.0 |

The above production is repeated using toluene instead of acetic acid as the solvent. In this case, the toluene solution after reaction is washed with water, dried over a drying agent, and evaporated under reduced pressure to afford an oily residue. This is crystallised from a suitable solvent to afford crystals of the product whose formula is given above.

EXAMPLES 7–13

In an analogous manner to that described in Example 6, the following compounds of formula I are produced from the appropriate starting materials.

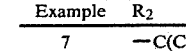

| Example | $R_2$ | $R_3$ | $R_4$ |
|---|---|---|---|
| 7 | —C(CH$_3$)$_3$ | —C(CH$_3$) | H |
| 8 | —C(CH$_3$)$_3$ | —C(CH$_3$)$_3$ | —CH$_3$ |
| 9 | —C(CH$_3$)$_3$ | H | —CH$_3$ |
| 10 | —CH(CH$_3$) (C$_2$H$_5$) | H | H |
| 11 | —C(CH$_3$)$_3$ | H | H |
| 12 | 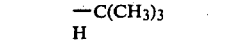 | H | H |
| 13 |  | H | H |

APPLICATION EXAMPLE

A sample of polypropylene which has been stabilized with 0.1% of the tetra ester of β-(3,5-di-tert.-butyl-4-hydroxyphenyl)propionic acid and pentaerythritol and with 0.1% calcium stearate ("base-stabilized polypropylene") is mixed with 0.2% of the compound of Example 1 at 170° for 5 minutes using a laboratory rolling mill (Schwabenthan). The resulting polypropylene product is submitted to a melt flow index determination at 2.16 Kp/230° according to the American Standard Test Method (ASTM) D-1238-70.

The above procedure is repeated using 0.2% of the compound of Example 2 in place of 0.2% of the compound of Example 1, and unstabilized polypropylene and base-stabilized polypropylene samples are also submitted to the melt flow index determination.

The results are presented in the following table.

| Polypropylene Sample | Melt flow Index at 2.16 Kp/230° |
| --- | --- |
| unstabilized | 25 |
| base-stabilized | 15.0 |
| base-stabilized and with 0.2% of compound of Example 1 incorporated | 3.1 |
| base-stabilized and with 0.2% of compound of Example 2 incorporated | 3.0 |

What is claimed is:

1. A compound of formula I',

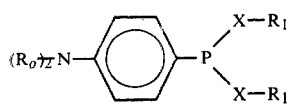   I' wherein
each $R_o$, independently, is $(C_{1-8})$ alkyl, the aggregate of the carbon atoms in the two alkyl groups not exceeding 10;
each X, independently, is oxygen or sulfur; and
each $R_1$, independently, is $(C_{4-18})$ alkyl; unsubstituted phenyl or phenyl substituted by 1 to 3 substituents selected from 1 to 3 $(C_{1-9})$ alkyl groups, said alkyl groups having an aggregate of carbon atoms not exceeding 12, a cyclohexyl group, an unsubstituted phenyl group and a mono-$(C_{1-4})$ alkyl-substituted phenyl group.

2. A compound according to claim 1 of formula I'',

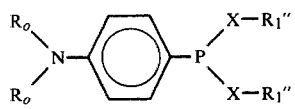   I'' in which
each $R_o$ and each X, independently, is as defined in claim 1,
and each $R_1''$, independently, is $(C_{4-18})$ alkyl, unsubstituted phenyl or phenyl substituted with 1 to 3 $(C_{1-9})$ alkyl groups, said alkyl groups having an aggregate of carbon atoms not exceeding 12.

3. A compound according to claim 1, in which each $R_o$ is the same, each X is the same and each $R_1$ is the same.

4. A compound according to claim 1 of the formula

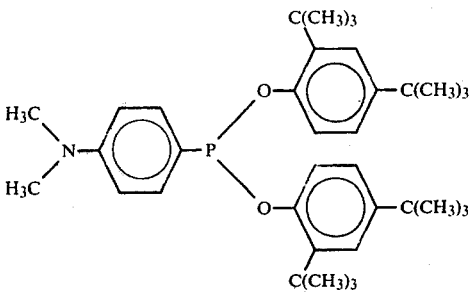

of the formula

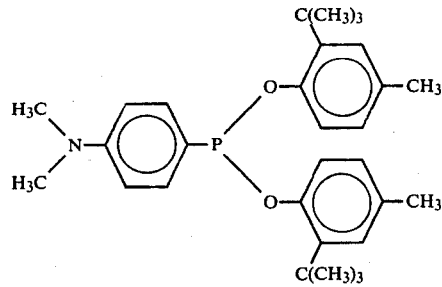

of the formula

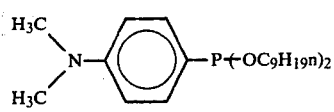

of the formula

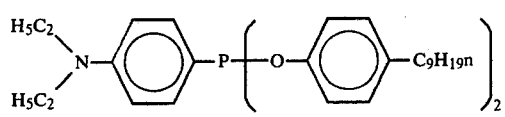

or of the formula

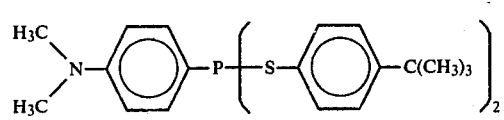

* * * * *